(12) United States Patent
Madden

(10) Patent No.: US 10,632,021 B2
(45) Date of Patent: Apr. 28, 2020

(54) NURSING PAD

(71) Applicant: Kathleen A. D. Madden, Calabafas, CA (US)

(72) Inventor: Kathleen A. D. Madden, Calabafas, CA (US)

( * ) Notice: Subject to any disclaimer, the term of this patent is extended or adjusted under 35 U.S.C. 154(b) by 76 days.

(21) Appl. No.: 15/494,389

(22) Filed: Apr. 21, 2017

(65) Prior Publication Data

US 2018/0168872 A1 Jun. 21, 2018

Related U.S. Application Data

(63) Continuation-in-part of application No. 14/072,550, filed on Nov. 5, 2013, now abandoned, which is a continuation-in-part of application No. 13/317,137, filed on Oct. 11, 2011, now abandoned.

(60) Provisional application No. 61/404,905, filed on Oct. 12, 2010.

(51) Int. Cl.
| | |
|---|---|
| *A61F 13/14* | (2006.01) |
| *A61F 13/515* | (2006.01) |
| *A41C 3/04* | (2006.01) |
| *A61F 13/536* | (2006.01) |
| *A61F 13/514* | (2006.01) |
| *A61F 13/513* | (2006.01) |
| *A61F 13/15* | (2006.01) |

(52) U.S. Cl.
CPC .............. *A61F 13/141* (2013.01); *A41C 3/04* (2013.01); *A61F 13/515* (2013.01); *A61F 13/51456* (2013.01); *A61F 13/536* (2013.01); *A61F 2013/15016* (2013.01); *A61F 2013/1591* (2013.01); *A61F 2013/15869* (2013.01); *A61F 2013/51355* (2013.01)

(58) Field of Classification Search
CPC ...... A61F 13/14; A61F 13/141; A61F 13/515; A61F 13/533; A61F 13/536; A61F 2013/15016; A61F 2013/5326; A41C 3/04
See application file for complete search history.

(56) References Cited

U.S. PATENT DOCUMENTS

| | | | | |
|---|---|---|---|---|
| 3,442,268 A | * | 5/1969 | Bird | A61F 13/141 604/380 |
| 5,104,396 A | * | 4/1992 | Oatley | A61F 13/532 604/379 |
| 5,683,286 A | * | 11/1997 | Kielland | A61F 13/141 2/267 |
| 6,074,272 A | * | 6/2000 | Hebert | A61F 13/141 450/37 |
| 6,419,548 B1 | * | 7/2002 | Wittes | A41C 3/065 2/267 |
| 8,628,507 B1 | * | 1/2014 | Carroll | A61F 13/141 604/346 |

(Continued)

*Primary Examiner* — Catharine L Anderson
(74) *Attorney, Agent, or Firm* — Michael J. Foycik, Jr.

(57) ABSTRACT

A disposable nursing pad has one embodiment with three layers which before use are flat, and in use become cup-shaped. The first layer is an outermost layer, the second layer is a middle layer, and the third layer is an innermost layer. The outermost layer and the innermost layer are disk-shaped. The middle layer has a central body portion and a plurality of arms extending outwardly in a generally spiral pattern. Regions of the first and third layers between the spiral arms can be folded to allow contouring of the liner to the body of a nursing mother.

8 Claims, 8 Drawing Sheets

(56) References Cited

U.S. PATENT DOCUMENTS

2008/0294136 A1\* 11/2008 Kawakami ............ A61F 13/141
604/385.07
2014/0188090 A1\* 7/2014 Riesinger .............. A61F 13/066
604/543

\* cited by examiner

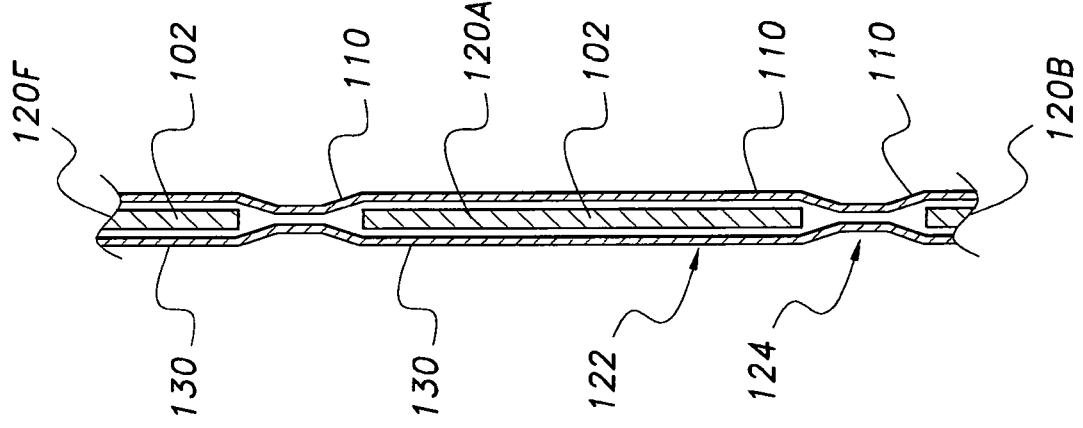
FIG. 8
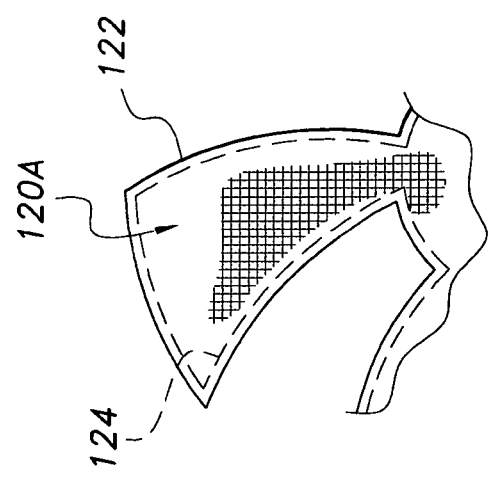
FIG. 7
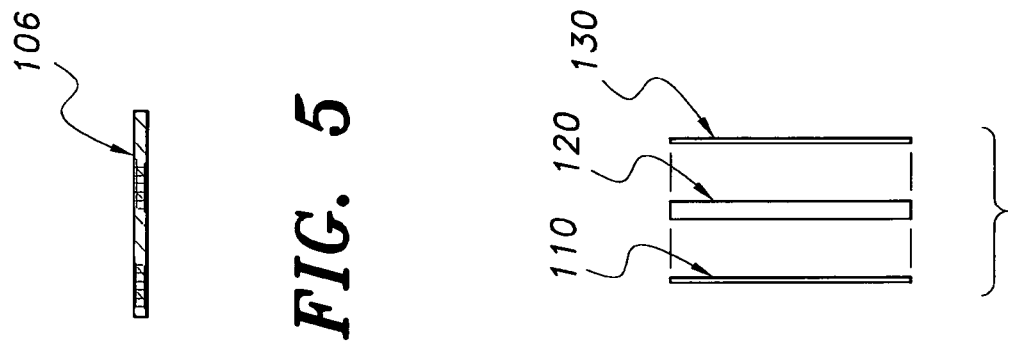
FIG. 5
FIG. 6

NURSING PAD

CROSS REFERENCE TO RELATED APPLICATIONS

This invention is a continuation in part of prior U.S. utility patent application Ser. No. 14/072,550 on Nov. 5, 2013, entitled Brassiere Liner, for inventor Kathleen A. D. Madden, which in turn claims priority of continuation in part of prior U.S. utility patent application Ser. No. 13/317,137 filed on Oct. 11, 2011, entitled Brassiere Liner, for inventor Kathleen A. D. Madden, which in turn claims priority of U.S. Provisional patent application Ser. No. 61/404,905 filed on Oct. 12, 2010, entitled Brassiere Liner for inventor Kathleen A. D. Madden; and the entire disclosures thereof are incorporated herein by reference thereto.

The entire specification and drawings of U.S. Pat. No. 5,690,536, issued to Kathleen A. D. Madden on Nov. 25, 1997, is hereby referred to and incorporated herein in its entirety.

STATEMENT REGARDING FEDERALLY SPONSORED RESEARCH OR DEVELOPMENT

Not applicable.

FIELD OF THE INVENTION

This invention relates to multi-layer disposable nursing pads for nursing mothers. More specifically, the nursing pads maintain their shape and positioning while being worn and prevent breast milk leakage from seeping into and through a mother's clothing.

BACKGROUND OF THE INVENTION

Devices for preventing breast milk leakage from contacting and seeping into and through clothing are currently available on the market. Generally, these devices fall into two broad categories, nursing or breast pads and nursing or protective brassieres. These two broad categories each comprise two general sub-categories, reusable pads and disposable pads, and unitary brassieres and brassieres having replaceable absorbent pads. Each of the devices currently comprising these categories suffers from at least one disadvantage, including low moisture absorbency, visibility of the device through clothing, bulkiness, inability to keep the moisture of the breast milk away from both the skin and clothing, poor fit within the brassiere, failure to maintain the proper shape within the brassiere, and lack of multiple sizes for accommodating women's differently sized breasts.

In addition, the prior art devices use large pads for absorbing liquid, and cannot conform easily to different cup shapes and sizes.

SUMMARY OF THE INVENTION

From the foregoing, it is seen that it is a problem in the art to provide a device meeting the above requirements. According to the present invention, a device is provided which meets the aforementioned requirements and needs in the prior art. Specifically, the device according to the present invention provides a disposable nursing pad that has three layers which before use are flat, and in use become cup-shaped. The first layer is an outermost layer, the second layer is a middle layer, and the third layer is an innermost layer which in use is in contact with the skin of the user. The outermost layer and the innermost layer have circular peripheries and are generally disk-shaped. A middle layer has a non-circular periphery, and has a central body portion and a plurality of arms extending outwardly in a generally spiral pattern.

In this nursing pad, the outermost extent of the plurality of arms is not further than the outermost periphery of the outermost and innermost layers. At least the outermost layer and the innermost layer are attached together, securing the middle layer between them. The first, outermost layer is formed of a moisture resistant layer. The second, middle layer is absorbent, and absorbs liquids. This second layer can be retained between the first and third layers which are attached to each other; or the second layer can itself be attached to either or both of the first and third layers. The third layer is a wicking layer having wicking material for wicking away moisture into the second, middle absorbent layer.

Regions of the first and third layers located between the spiral arms, when applied against the breast in use, become folded so as to allow contouring of the liner to the body of the user.

The specific shape used, having spaced-apart arms extending in a generally curved pattern, has at least the following advantages, which are a significant improvement over the prior art: (1) they permit instant adaptation to a wider variety of sizes and shapes; (2) the spiral pattern uses less material without sacrificing thoroughness of coverage since the spiral arms converge when the pad is applied in use; (3) the spiral pattern means that, in use, leaks are stopped in every direction—if the arms were straight there would be uneven leakage control; and (4) the first and third layers can be directly bonded together in the regions between the spiral arms of the middle layer.

Other objects and advantages of the present invention will be more readily apparent from the following detailed description when read in conjunction with the accompanying drawings.

BRIEF DESCRIPTION OF THE DRAWINGS

FIG. 5 is a sectional view of the middle layer, taken along line 5-5 of FIG. 2.

FIG. 6 is an assembly view of the outer, middle, and inner layers of FIGS. 1-5.

FIG. 7 shows a close up view of a portion of the bra cup liner of FIG. 1 showing two types of stitching used to connect the outer and inner layers of FIG. 1.

FIG. 8 is a schematic sectional view of the assembled layers of the bra cup liner of FIG. 1, showing connection between the inner and outer layers.

DETAILED DESCRIPTION OF THE INVENTION

Figure 1:
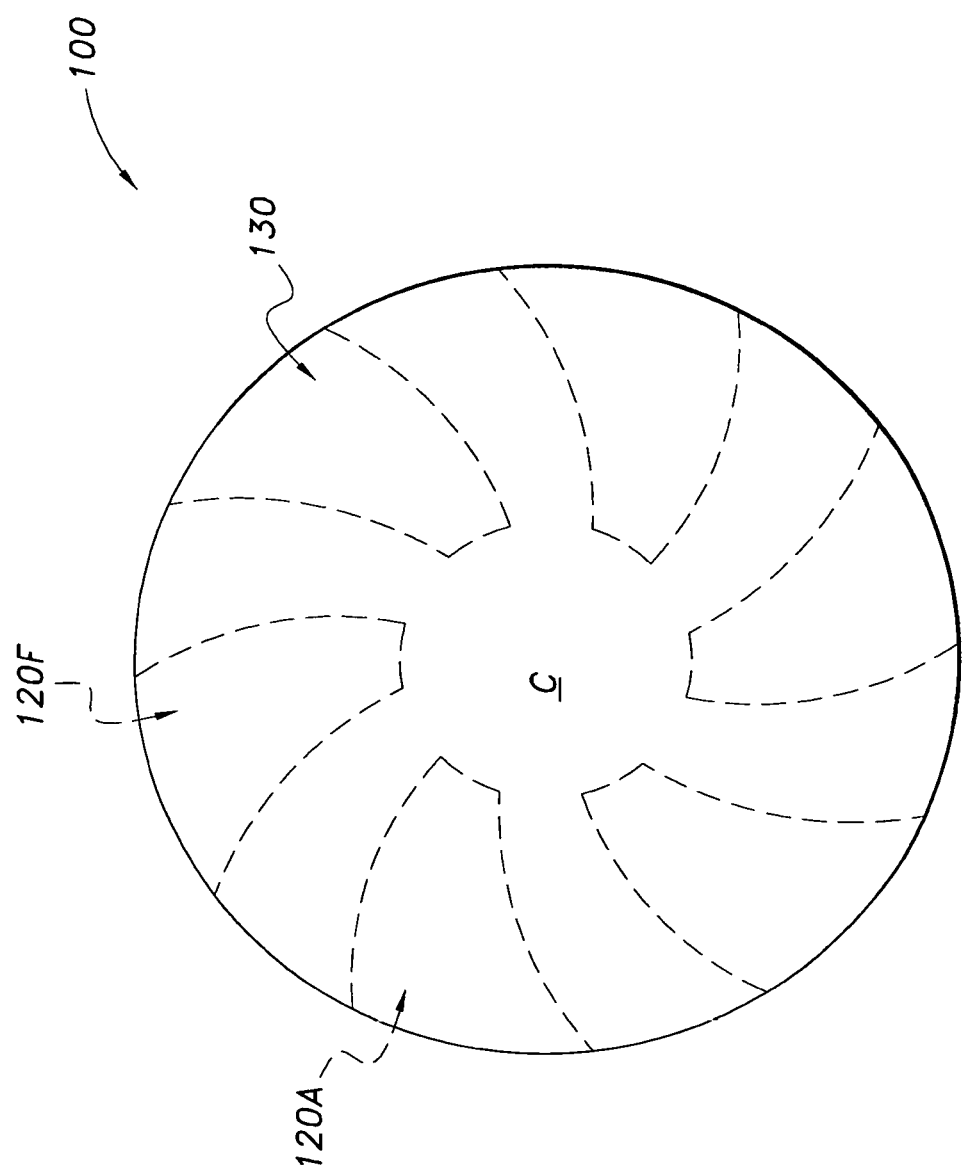
FIG. 1 is a schematic drawing of a bra cup liner in its initial configuration, showing an inner, wicking layer in elevational view and showing an absorbent middle layer in dashed outline, according to the present invention.

FIG. 1 is a schematic drawing of a bra cup liner 100 in its initial configuration, showing an inner, wicking layer 130 in elevational view having a center C, and showing an absorbent middle layer 120 (shown in FIG. 2) in dashed outline. The middle layer 120 has a plurality of spiral-shaped arms 120A-F (shown in FIG. 2), including arms 120A and 120F identified and shown in FIG. 1. The nursing pad 100 is shown flat in FIG. 1, its configuration prior to use, and in use it is cup-shaped to conform comfortably to the shape of the mother's breasts. To use the nursing pad 100, it is simply inserted into the cup of a bra (not shown), and the regions of the nursing pad 100 in between the spiral arms 120A-F can fold or wrinkle so as to allow the spiral arms 120A-F to converge together. The inner layer 130 in use is proximal to the skin of the user, and wicks away breast milk leakage from the mother's skin into the second intermediate absorbent layer 120 of FIGS. 1 and 2.

Specifically, the device of FIGS. 1-10 provides a disposable nursing pad which has three layers 110, 120, and 130 which before use are flat, and in use become cup-shaped. The first layer 110 is an outermost layer, the second layer 120 is a middle layer, and the third layer 130 is an innermost layer. The outermost layer 110 and the innermost layer 130 have circular peripheries and are generally disk-shaped. The middle layer 120 has a non-circular periphery, and has a central body portion 106 (shown in FIG. 2) and a plurality of arms 120A-F extending outwardly in a generally spiral pattern (also shown in FIG. 2).

In this nursing pad 100, the outermost extent of the plurality of arms 120A-F is not further than the outermost periphery of the outermost layer 110 and the innermost layer 130. At least the outermost layer 110 and the innermost layer 130 are attached together, securing the middle layer 120 between them. The first, outermost layer 110 is formed of a moisture resistant material. The second, middle layer 120 is absorbent, and absorbs liquids. This second layer 120 can be retained between the first layer 110 and the third layer 130 which are attached to each other; or the second layer 120 can itself be attached to either or both of the first and third layers 110 and 130. The third layer 130 is a wicking layer having wicking material for wicking away moisture into the second, middle absorbent layer 120. Regions 104 (shown in FIG. 10) between the spiral arms 120A-F, in use become folded to allow contouring of the nursing pad 100 to the body of the user.

The specific shape used, having spaced-apart arms 120A-F extending in a generally curved pattern, has at least the following advantages, which are a significant improvement over the prior art: (1) they permit instant adaptation to a wider variety of sizes and shapes; (2) the spiral pattern uses less material without sacrificing thoroughness of coverage since the spiral arms 120A-F converge when the pad 100 is applied in use; (3) the spiral pattern means that, in use, leaks are stopped in every direction—if the arms 120A-F were straight instead of being curved then there would be uneven leakage control; and (4) the first and third layers 110 and 130 can be directly bonded together in the regions between the spiral arms of the middle layer, permitting ease of manufacture.

Figure 2:
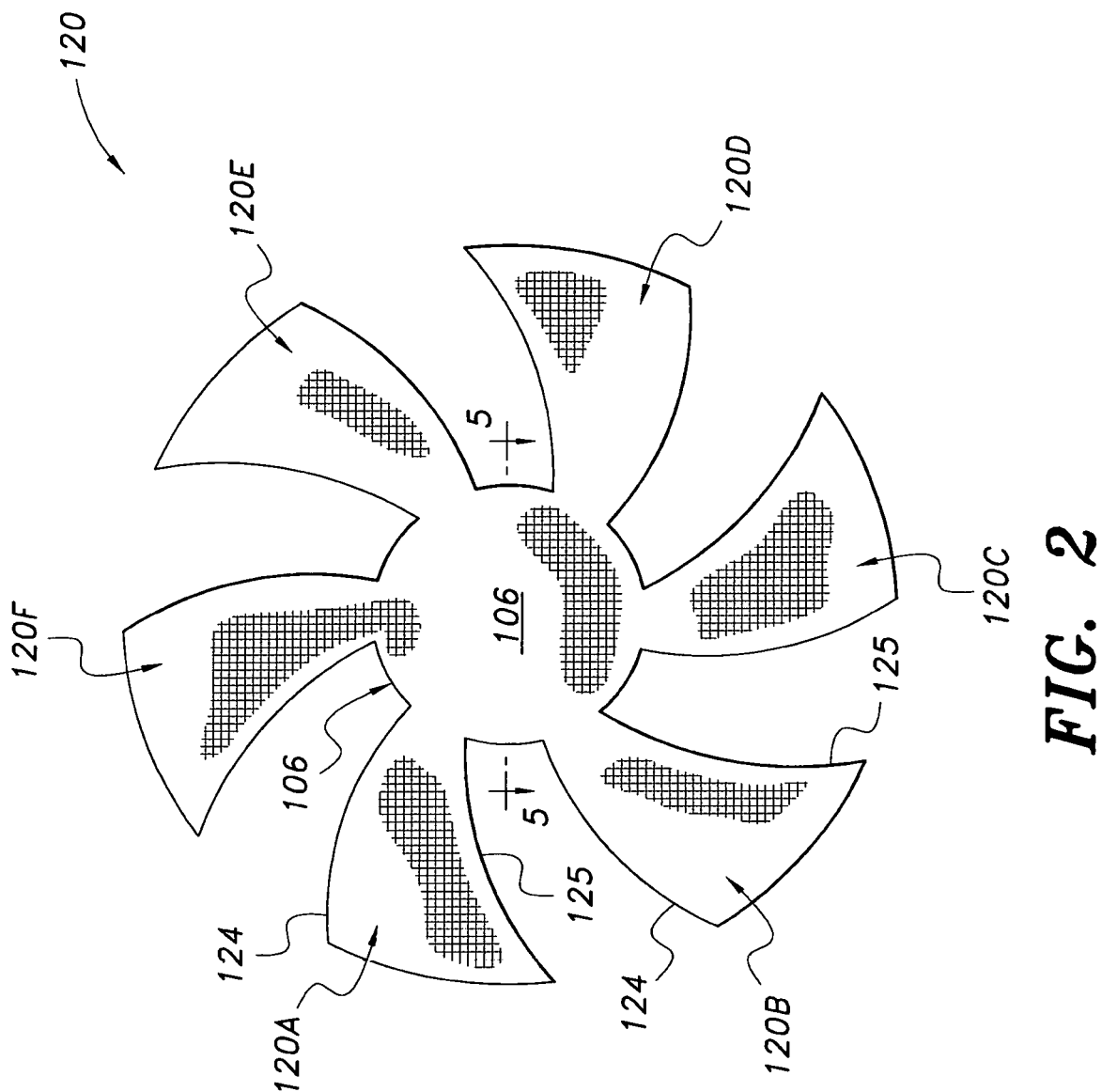
FIG. 2 is a top elevational view of the middle layer of FIG. 1.

FIG. 2 is a top elevational view of the middle layer 120 of FIG. 1. This view shows a central region 106 which is generally circular, and having a plurality of spiral-shaped arms 120A, 120B, 120C, 120D, 120E, and 120F extending from the central region 106. While six spiral arms 120A-F are shown, it will be understood that a greater or lesser number of spiral arms can be used without departing from the present invention. For example, five, seven, eight, or nine spiral arms could be used.

Figure 3:
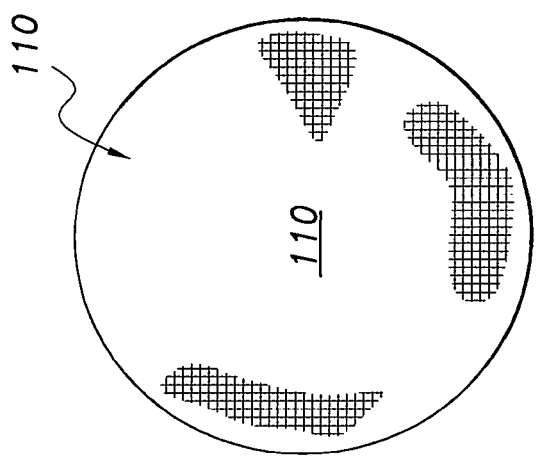
FIG. 3 is a top elevational view of an outer, moisture resistant layer which underlies the middle layer shown in FIG. 1, shown by itself.

FIG. 3 is a top elevational view of an outer, moisture resistant layer 110 which underlies the middle layer shown in FIG. 1. In use, the middle layer 110 is the most distal layer from the skin of the user.

Figure 4:
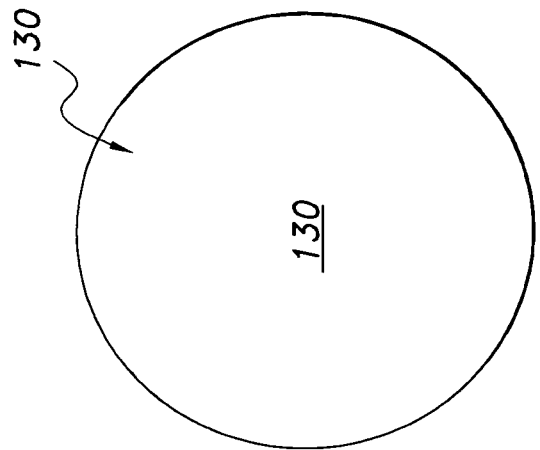
FIG. 4 is a top elevational view of the inner layer of FIG. 1, shown by itself.

FIG. 4 is a top elevational view of the inner layer 130 of FIG. 1, and is described hereinabove with regard to FIG. 1. The layer 130 is a wicking layer which in use is proximal to and in contact with the skin of the user. The layer 130 is composed of any type of known wicking materials which can conduct moisture to the middle layer 120 and which are suitable for use in contact with human skin. Such materials are well known in the art, such as in multi-layer absorbent diapers and in conventional prior bra cup liners.

FIG. 5 is a sectional view of the central disk portion 106 of the middle layer 120, taken along line 5-5 of FIG. 2. Here, it is seen that the material is a fibrous, absorbent material. Any known type of absorbent material can be used, including materials such as those used in the prior art absorbent disposable diapers. Selection of such materials is within the ambit of skill of any one having skill in the absorbent liner arts or in the disposable diaper arts. All such absorbent materials suitable for use with human skin are contemplated as being within the scope of the present invention.

FIG. 6 is an assembly view of the outer layer 110, the middle layer 120, and the inner layer 130 of FIG. 1.

FIG. 7 shows a close up view of a portion of the bra cup liner 100 of FIG. 1 showing two types of stitching 122 and 124, used to connect the outer layer 110 and the inner layer 130 of FIG. 1. The stitching 124 passes through all three layers 110, 120, and 130, securing them to each other. The stitching 122 passes only through the innermost layer 130 and the outermost layer 110, missing the layer 120 entirely. Either type of stitching can be used alone or in combination, and other stitching patterns can be used.

Instead of stitching, ultrasonic welding can be used, in which case the layers 110 and 130 are secured together easily and securely, without need for any stitching. Alternatively, adhesive can be used in the pattern of the stitching 122. Such adhesives and securing methods would be understood by any one having skill in the manufacturing or sewing arts. All such types and methods of securing the layers 110 and 130 together are contemplated as being within the scope of the present invention. Further, it is contemplated that all three layers 110, 120, and 130 can be bonded together, by any suitable adhesive, ultrasonic welding, stitching, fastening, or other connection means. Such connection means would be known by any one having skill in the fastening, welding, adhesive, or sewing arts, and all such connection means are contemplated as being within the scope of the present invention.

FIG. 8 is a schematic sectional view of the assembled layers 110, 120, and 130 of the bra cup liner 100 of FIG. 1, showing connection between the inner, proximal layer 130 and the outer, distal layer 110, as well as the stitching 122 and 124 of FIG. 7. This view is schematic and the parts are expanded and distances between elements exaggerated for the sake of clarity.

Figures 9, 10:
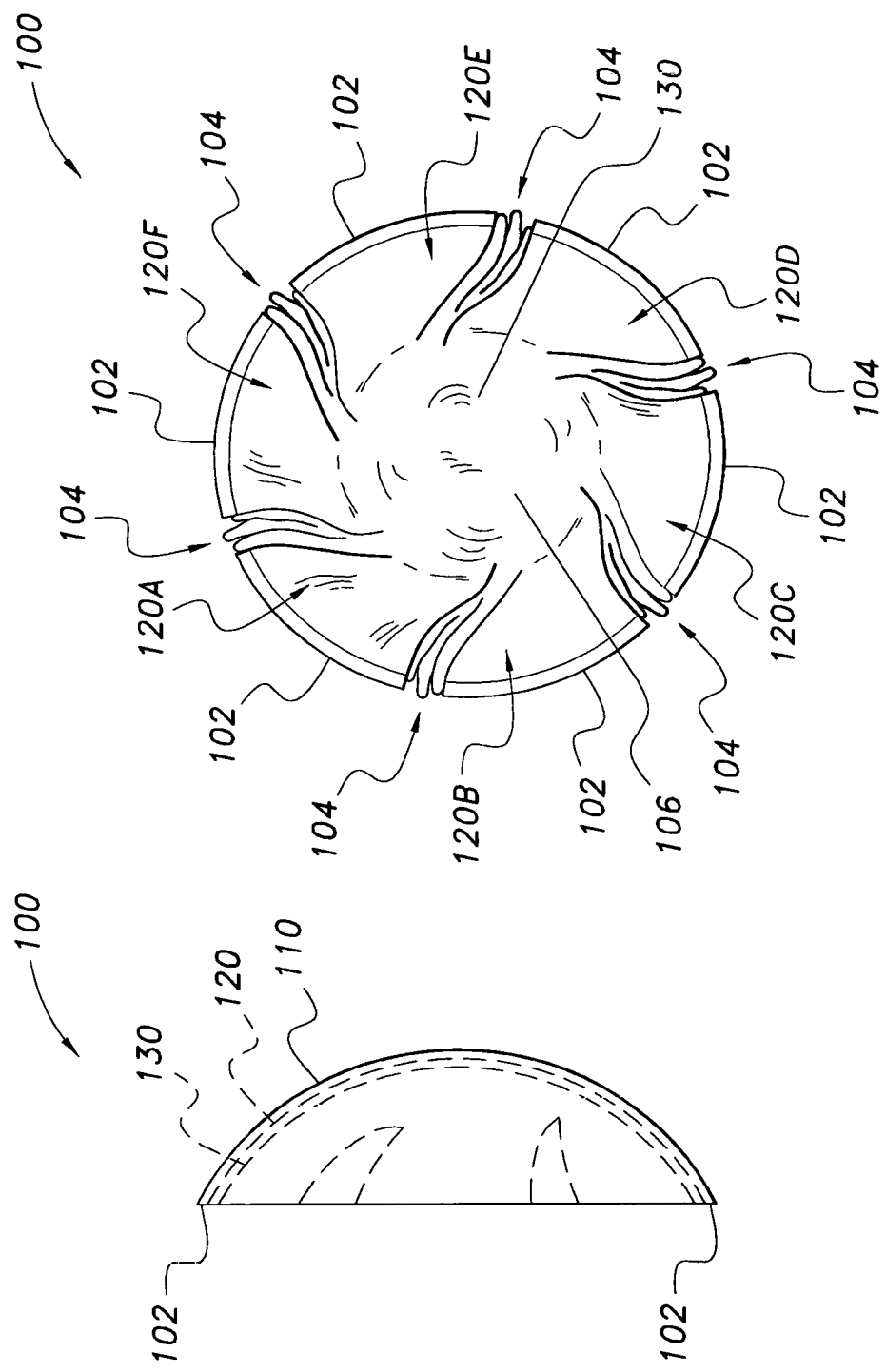
FIG. 9 shows a side elevational view of the bra cup liner of FIG. 1 in use, having a curved shape.
FIG. 10 shows a front elevational view of the bra cup liner of FIG. 1 in use, showing the folds which occur during convergence of the arms of the middle layer in forming the curved shape of FIG. 9.

FIG. 9 shows a side elevational view of the bra cup liner 100 of FIG. 1 in use, having a curved shape. The layers 120 and 130 are shown in dashed outline. The outer, distal layer 110 is the only layer visible in elevation in FIG. 9, the layers 120 and 130 being shown in dashed outline. The periphery is shown at numeral 102 in FIG. 9.

FIG. 10 shows a front elevational view of the bra cup liner 100 of FIG. 1 in use, showing the folds 104 which occur during convergence of the spiral arms 120A-F of the middle layer 120 in forming the curved shape of FIG. 9. In this view, only the innermost, proximal layer 130 is visible in elevation; the location of some other regions are indicated schematically for the sake of clarity such the as central region 106 of layer 120 and the location of the spiral arms 120A-F. The periphery 102 is visible in elevation in this view.

While six spiral-shaped arms 120A-F are shown, it will be understood that the number can be different. For example, 5 spiral arms could be provided, or 7, 8, 9, or more such spiral arms can be provided. The spacing between the arms must be great enough to permit folds 104 to form when in use; this depends on the specific materials used and the thicknesses thereof, among other factors. All such variations are contemplated as being within the scope of the present invention.

Figure 11:
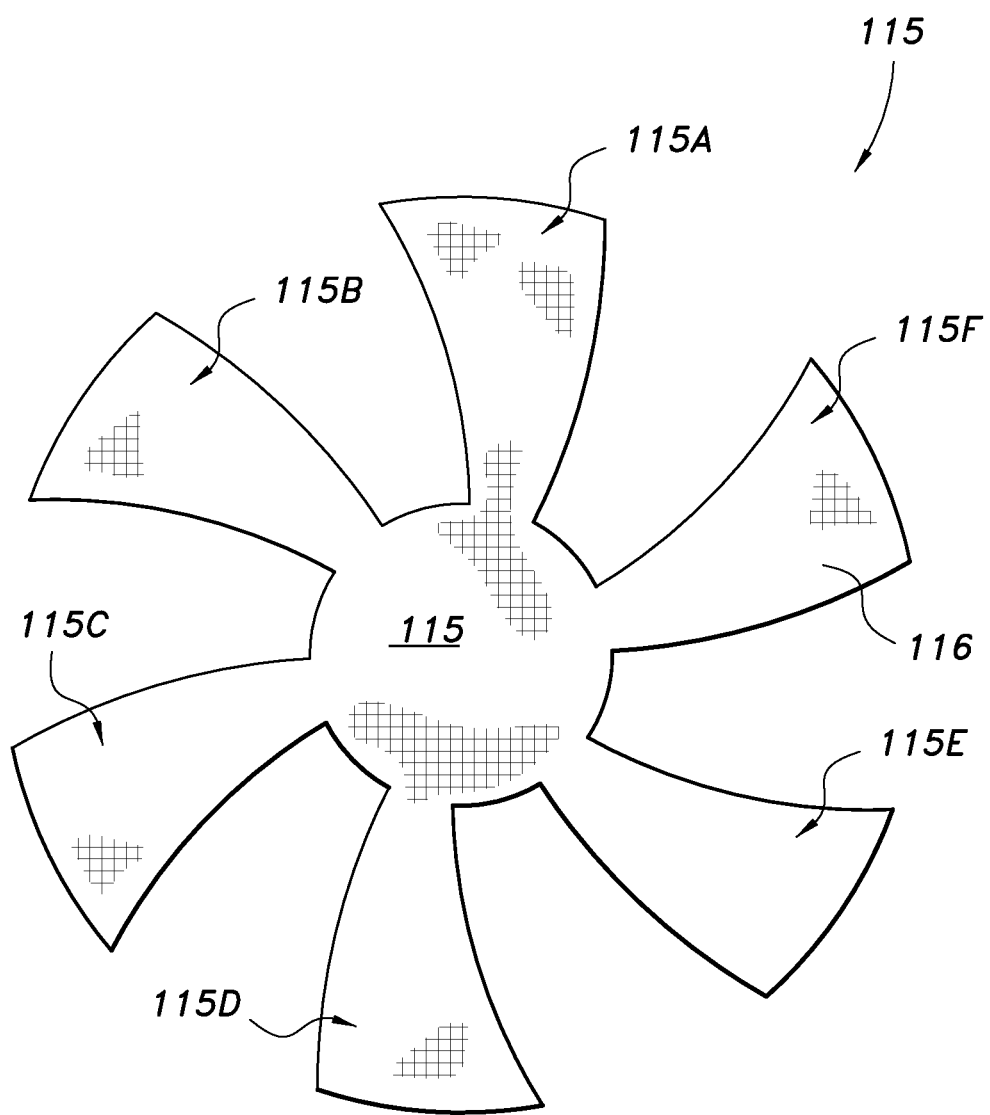
FIG. 11 is a top elevational view of a further layer used for structural support of the middle layer of FIG. 2.

FIG. 11 is a top elevational view of a further layer 115 used for structural support of the middle layer of FIG. 2. FIG. 11 is a further embodiment of the invention shown in FIGS. 1-10. The further layer 115 has a plurality of spiral-shaped arms 115A, 115B, 115C, 115D, 115E, and 115F. The further layer 115 is similar to the middle layer 120 of FIG. 2, and is provided in order to support the middle layer 120 when in use.

In use, the absorbent layer 120 may become heavy due to absorption of liquid, and could sag or lose its shape under those conditions. Also, the shape of the absorbent layer 120 can become deformed during storage or when handled; the further layer 115 is provided to maintain an attractive appearance of the assembly of layers forming the nursing pad of the present invention.

The fourth layer to this pad, namely further layer 115, maintains the shape of the absorbent layer 120 which is composed of fibrous, loose fill that may also contain a super absorbent substance such as is in most moisture absorbing products on the market today. For purposes of this discussion the absorbent layer 120 is believed to be a type that is included in most if not all nursing pads that are currently available for use by nursing mothers.

In this nursing pad embodiment, the further layer 115, denoted as a structural layer, is composed of a stiffened material which holds the shape of the absorbent layer (which may have loose fill) in the pinwheel-like shape between the two outer layers 110 and 130. The layer 130 wicks away moisture from the breast and the middle layer 120 contains the moisture within the pad to prevent leakage.

The further layer 115 can be composed of any relatively thin, somewhat flexible material that does not sag or become distorted when wet. The thickness of the further layer 115 depends on the structural properties of the material being used; a very strong material can be relatively thin, whereas a weaker material would need to be relatively thicker. Many materials have such structural properties, including stiffened felt, molded plastic, stiffened cloth, and/or any combination of materials which are known to any one having skill in the brassiere arts or garment arts.

The further layer 115 can be attached to the middle layer 120 by adhesive or by stitching, or other means known to any one having skill in the garment arts or fastening arts.

Figure 12:
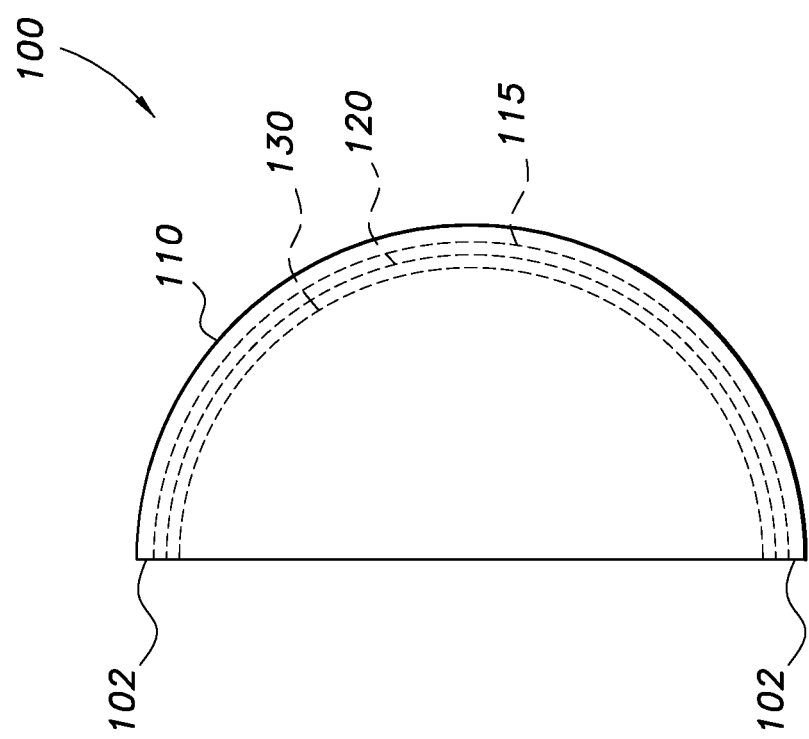
FIG. 12 shows a side elevational view of the bra cup liner having the embodiment shown in FIG. 11 when in use, having a curved shape.

FIG. 12 shows a side elevational view of the bra cup liner having the embodiment shown in FIG. 11 when in use, having a curved shape. The layers are as indicated.

Figure 13:
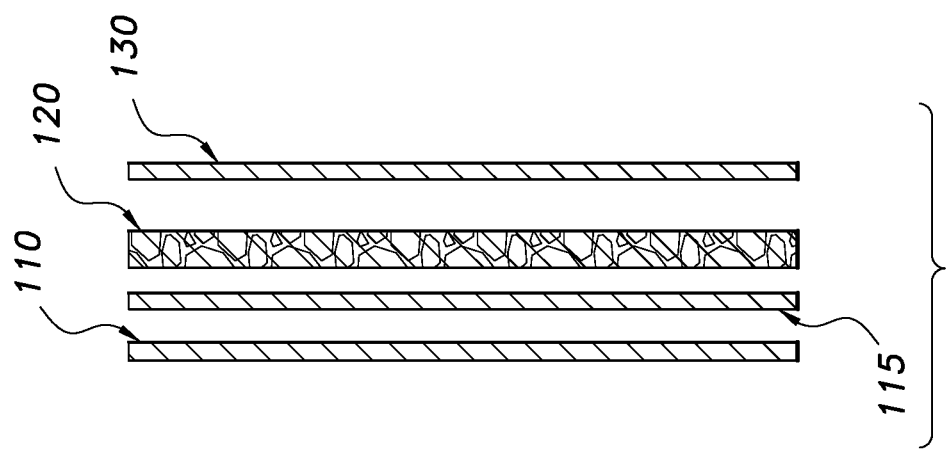
FIG. 13 is an assembly view of the outer layer, the further layer of FIG. 11, the middle layer, and inner layer, according to the embodiment shown in FIGS. 11 and 12.

FIG. 13 is an assembly view of the outer layer 110, the further layer 115 of FIG. 11, the middle 120 layer, and inner layer 130, according to the embodiment shown in FIGS. 11 and 12.

The arms 120A-120F extend a fixed distance from a center point of the central body portion 106, referred to hereafter as an arm radius. In of preferred embodiment, the central body portion 106 of the second layer 120 has a radius that is in a range between 25 percent and 40 percent of the arm radius.

Each of the arms 120A-120F is curved in a spiral shape as shown in FIG. 2, and are all curved in the same direction. The arms 120A-120F are preferably substantially uniformly spaced, and occupy an area hereafter referred to as a first area. Spaces exist between adjacent ones of the arms 120A-120F. In a preferred embodiment, these spaces occupy a surface area that is hereafter referred to as a second area.

In the preferred embodiment, the second area has a magnitude in a range between 50 percent of the first area and 100 percent of the first area.

There are preferably six arms 120A-F in this preferred embodiment. Additional arms can be used, up to 8 total arms.

Figure 14:
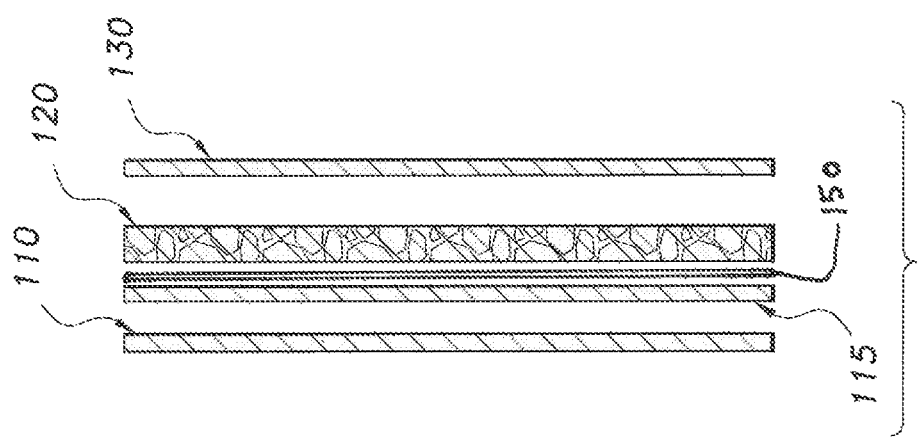
FIG. 14 shows a further embodiment of the invention, and illustrates five layers in cross section.

FIG. 14 shows a further embodiment of the invention, and illustrates five layers in cross section. The layers 110, 115, 120, and 130 are as discussed hereinabove. A fifth layer 150 is provided, as follows.

The fifth layer 150 is a secondary absorbent layer that is composed of an absorbent polyacrylate coated fabric that will, unlike the other absorbent layers known in the prior art, will pull fluid from the second layer 120 (which is composed of absorbent material) and hold it away from the skin. This fifth layer, while being absorbent. Also provides additional support.

Figure 15:
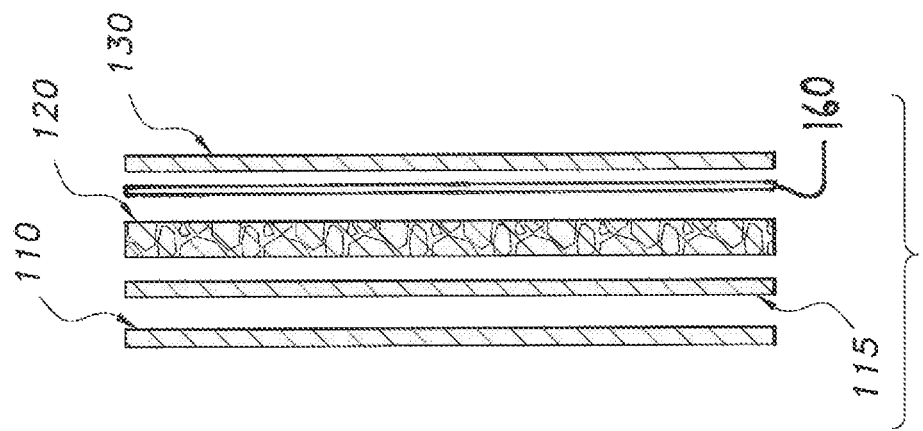
FIG. 15 shows a further embodiment of the invention, and illustrates five layers in cross section.

FIG. 15 shows a further embodiment of the invention, and illustrates five layers in cross section. The layers 110, 115, 120, and 130 are as discussed hereinabove. A fifth layer 160 is provided, as follows.

The fifth layer 160 is a secondary absorbent layer that is composed of an absorbent polyacrylate coated fabric that will, unlike the other absorbent layers known in the prior art, will pull fluid from the second layer 120 (which is composed of absorbent material) and hold it away from the skin. This fifth layer, while being absorbent. Also provides additional support.

Additionally, the fifth layer 160 has a sprinkling of very fine particles of an antacid powder adhered thereto. In some cases, the nursing mother produces acidic milk that can damage clothing and other fabrics that come into contact with the nursing pad during or after use. It is believed that consumption of some foods increases the acidity of the mother's milk, and therefore the layer 160 can neutralize the acidity in the mother's milk as it is being absorbed.

The invention being thus described, it will be evident that the same may be varied in many ways by a routineer in the applicable arts. Such variations are not to be regarded as a departure from the spirit and scope of the invention and all such modifications are intended to be included within the scope of the claims.

What is claimed is:

1. A nursing pad conforming to an interior of a bra cup to prevent leakage during use by a nursing mother, comprising:

a liner body composed of a first layer, a further layer, a second layer, and a third layer; said first layer being adjacent to said further layer; said second layer being adjacent to said further layer; and said third layer being adjacent to said second layer;

said liner body having an initial flat condition and a folded condition during use;

said first layer having an initial flat circular shape, said first layer being composed of a moisture resistant material; and said first layer in use being an outer layer adapted to contact the clothing of a nursing mother;

said further layer being a structural member for providing structural support to said second layer;

said second layer having an initial flat shape with a central solid region and a plurality of spaced-apart arms extending from said central solid region; each of spaced-apart arms extending in a generally spiral shape in a same spiral direction whereby an initial spacing exists between adjacent ones of said spaced-apart arms, said plurality of spaced-apart arms extending in said generally spiral shape respectively being spiral-shaped arms; said second layer being composed of an absorbent layer adapted to absorb liquids;

said initial spacing forming spaces between said spaced apart arms forming a spiral pattern which is substantially equal in size and shape as said spiral shape formed by said spaced apart arms;

said third layer having an initial flat circular shape substantially coextensive in size with said first layer; said third layer being composed of a wicking material; and said third layer being adapted for use in contacting the skin of a nursing mother;

said second layer being secured between said first layer and said third layer, in which first regions of said first and said third layers are adjacent said spaced-apart arms of said second layer and in which the remaining regions of said first layer and said third layer constitute second regions that are not in contact with said spaced-apart arms;

in said folded condition of said liner body during use, said liner body is folded to conform to an interior of a bra cup by bending of said first, said second and said third layers such that said liner body becomes generally cup-shaped; in said folded condition said remaining regions of said first layer and said third layer being folded so as to permit said spacing between said spiral-shaped arms to become reduced in said folded condition of said liner relative to said spacing between said spiral-shaped arms in said flat condition;

said central solid region of said second layer having a center point and a first radius from said center point; and wherein said plurality of spaced-apart arms of said second layer extend a fixed distance from said center point which is an arm radius; wherein said first radius of said second layer has a magnitude that is in a range of between 25 percent and 40 percent of said arm radius;

wherein said spiral-shaped arms are substantially uniformly spaced, and occupy a first area; and wherein spaces exist between adjacent ones of said spiral-shaped arms which occupy a second area; and wherein said second area has a magnitude in a range between 50 percent of said first area and 100 percent of said first area;

whereby said spiral-shaped arms of said liner body when in said folded condition form an absorbent cup-shaped barrier to liquid leakage such that liquid flowing in between adjacent ones of said spiral-shaped arms under the force of gravity will eventually encounter at least one of said second spiral-shaped arms.

2. A nursing pad as claimed in claim 1, wherein said first layer and said third layer are secured together by stitching.

3. A nursing pad as claimed in claim 2 wherein said stitching does not pass through said second layer.

4. A nursing pad as claimed in claim 1, wherein said third layer and said first layer are secured together by adhesive.

5. A nursing pad as claimed in claim 1, wherein said third layer, said second layer, and said first layer are all secured together by adhesive.

6. A nursing pad as claimed in claim 1, wherein said third layer and said first layer are composed of material capable of being ultrasonically welded, and wherein said third layer and said first layer are secured together by ultrasonic welding.

7. A nursing pad as claimed in claim 1, further comprising a fifth layer disposed between said second layer and said further layer, wherein said fifth layer is a secondary absorbent layer that is composed of an absorbent polyacrylate coated fabric that will pull fluid from said second layer and hold it away from the skin; said fifth layer, while being absorbent, also provides additional support to said second layer.

8. A nursing pad as claimed in claim 1, further comprising a fifth layer disposed between said second layer and said third layer, wherein said fifth layer is a secondary absorbent layer that is composed of an absorbent polyacrylate coated fabric that will pull fluid from said second layer and hold it away from the skin; and said fifth layer having a sprinkling of antacid power adhered thereto, to neutralize acidity in fluid absorbed during use so as to prevent damage to clothing worn by the nursing mother.

* * * * *